United States Patent [19]

Monsimer et al.

[11] 4,205,060

[45] May 27, 1980

[54] MICROCAPSULES CONTAINING MEDICAMENT-POLYMER SALT HAVING A WATER-INSOLUBLE POLYMER SHEATH, THEIR PRODUCTION AND THEIR USE

[75] Inventors: Harold G. Monsimer, Norristown; Howard A. Bohm, Harleysville, both of Pa.

[73] Assignee: Pennwalt Corporation, Philadelphia, Pa.

[21] Appl. No.: 971,243

[22] Filed: Dec. 20, 1978

[51] Int. Cl.$^2$ .............................................. A61K 9/50
[52] U.S. Cl. ................................... 424/14; 252/316; 424/16; 424/19; 424/20; 424/21; 424/22; 424/323; 424/335; 424/78; 424/81
[58] Field of Search .................... 252/316; 424/14–38, 424/78–83

[56] References Cited

U.S. PATENT DOCUMENTS

| | | | |
|---|---|---|---|
| 3,608,063 | 9/1971 | Banker | 424/22 |
| 3,629,392 | 12/1971 | Banker et al. | 424/22 |
| 3,909,444 | 9/1975 | Anderson et al. | 252/316 |
| 4,016,254 | 4/1977 | Seager | 424/33 |

*Primary Examiner*—Shep K. Rose

[57] ABSTRACT

Microcapsules comprising a core containing a water-soluble salt of a medicament and a polymer, e.g., the salt of a medicament containing an amine-group and a carboxyl group containing polymer, and a sheath of a water-insoluble film forming polymer, e.g., ethyl cellulose, the method of their production and their administration are disclosed. The microcapsules can be formed by dispersing an aqueous solution of the medicament-polymer salt in a water-immiscible solvent solution of a water-insoluble film forming polymer, adding another water-immiscible solvent which is a non-solvent for the water-insoluble polymer, and collected the microcapsules. The microcapsules are administered orally to animals and exhibit substantially slower release rates and more uniform release rates in stomach acids than the corresponding unencapsulated salts or encapsulated non-polymeric salts.

5 Claims, 2 Drawing Figures

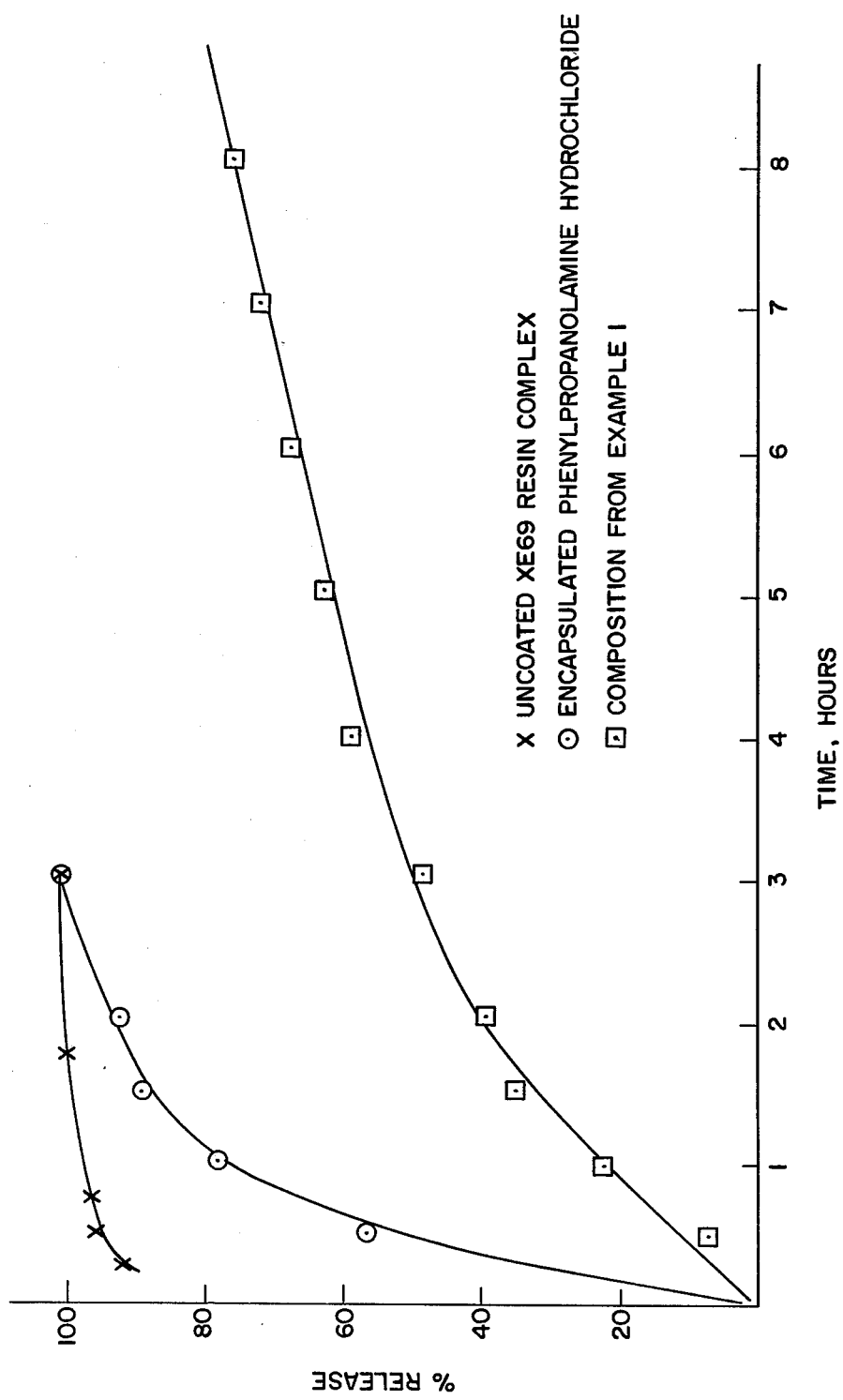

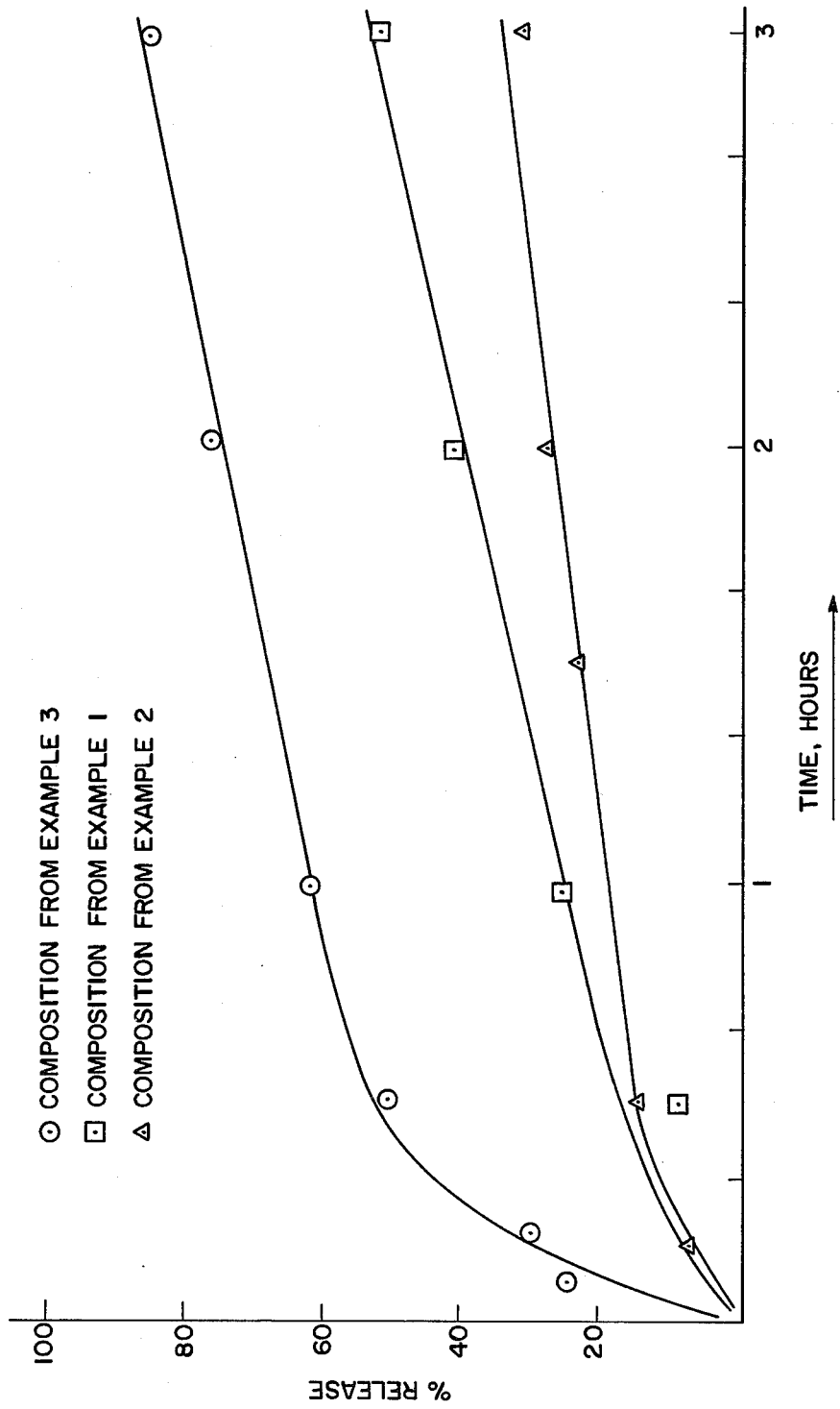

MICROCAPSULES CONTAINING MEDICAMENT-POLYMER SALT HAVING A WATER-INSOLUBLE POLYMER SHEATH, THEIR PRODUCTION AND THEIR USE

BRIEF SUMMARY OF THE INVENTION

This invention relates to microcapsules comprising a core containing a water-soluble salt of a medicament and a polymer, and a sheath of a film forming polymer. The microcapsules can be formed by dispersing an aqueous solution of the medicament-polymer salt in a water-immiscible solvent solution of a water-insoluble film forming polymer, adding another water-immiscible solvent which is a non-solvent for the water-insoluble polymer and collecting the microcapsules, e.g., by filtration. The microcapsules can also be formed by methods which are broadly known in the art.

The microcapsules of this invention are intended for oral administration to animals and exhibit substantially slower and more uniform release rates in stomach acids than the corresponding unencapsulated salts or encapsulated non-polymeric salts.

It is known in the art that the release rate of many medicaments can be retarded by forming a complex of a medicament containing appropriate functional groups with an ion exchange resin in particulate form. In particular, medicaments containing basic groups can be formed into delayed release compositions by complexing with appropriate ion exchange resins containing acid groups. Such complexes, in finely divided form, are activated by digestive juices and can be stored as aqueous suspensions. However, for many medicaments the release rate is too rapid to provide the 8 or more hours of useful delivery desired for an oral dosage form. Furthermore, such complexes release the medicament by a mechanism that is inherently first order. Therefore, the release rates decrease rapidly as the effective concentration of the residual medicament decreases. A partial proposed solution to the problem is the use of an initial low loading of medicament in order to take advantage of the flat end portion of the release curve (obtained by plotting the percentage of medicament released against time). However, low loading results in the waste of costly ion-exchange resin and, in some cases, unacceptably large dosage forms.

Another problem with known systems of medicament delivery utilizing ion exchange complexes is that the complexes are most economically prepared from commercial resins which are not generally available in the specific particle sizes needed to achieve a desired release rate. Since the release rate from a given unit weight of material is proportional to the total surface area which in turn varies with the cube of the radius (assuming the particles to be spherical) the shape, size and distribution of particles can be quite important in achieving a desired bulk release rate. Custom grinding and sorting add to the expense of the final products. Additionally, most ground materials are relatively large in particle size (approximately 50 microns) and irregular in shape. Coating or encapsulating of the particulate complexes has been utilized to improve the release rate but has added to the cost of the product.

In accordance with this invention microcapsules containing a medicament-salt complex are obtained having an extremely small particle size. The particle size is relatively uniform and reproducible. Because the particle size can be controlled the size can be used to control the bulk release rate.

An advantage of the microcapsules of this invention is that the uniformity of shape and decreased particle size result in a more palatable product. Moreover, particle size and shape are not determined by the availability of preformed insoluble ion exchange resins or by grinding or preparation of special resins by the user. Rather, under this invention particle size, and consequently release rate, can be controlled to a high degree.

Another advantage of this invention is that the formation of the medicament-polymer salt and subsequent encapsulation are carried out as one continuous process resulting in lower costs of raw materials and production relative to encapsulated ion-exchange resin complexes. Because both the complexing polymer and the medicament are in solution, the formation of the salt is almost instantaneous. Where solid resin is used, slow migration of the medicament into the complexing or salt forming resin frequently requires several hours.

Finally, the release of the medicament from the microcapsules of this invention is much slower and more uniform than obtained from unencapsulated ion-exchange resin complex or from encapsulated non-polymeric salt compositions.

BRIEF DESCRIPTION OF THE DRAWINGS

FIG. 1 is a graph comparing the release rate of microcapsules of this invention, an ion-exchange resin complex of the prior art and a microcapsule containing a non-polymeric salt of the same medicament.

FIG. 2 is a graph comparing the release rates of three different forms of microcapsules prepared in accordance with this invention.

DETAILED DESCRIPTION OF THE INVENTION

The microcapsules of this invention contain a water-soluble salt of a medicament having groups capable of salt formation with an appropriate polymer. For example, the medicament can contain basic groups such as amino groups which will form salts with a polymer containing acid groups, for example, carboxyl or sulphonic acid groups. Alternatively, the medicament can contain acid groups such as carboxyl or sulphonic acid groups and the basic salt-forming groups can be present in the polymer. Thus, the invention is applicable to a wide variety of medicaments, primarily those which are intended for oral administration. It is evident that upon contact with stomach acids the medicament will be released.

Among the medicaments suitable for use in this invention are phenylpropanolamine, dextromethorphan, ephedrine, pseudo-ephedrine, p-aminosalicylic acid, acetaminophen and chlorpheniramine.

Corresponding acid group containing polymers which can be mentioned include polyacrylic acid, water-soluble copolymers of acrylic acid and copolymerizable monomers, hydrolyzed copolymer of maleic anhydride and vinyl methyl ether, polymers or copolymers of maleic acid or fumaric acid, alginic acid, carboxymethylcellulose and polyvinylsulfonic acid. Where the medicament contains free acid groups analogous polymers containing free amino groups are suitable for formation of the medicament-polymer salt which comprises the core of the microcapsules of this invention. Since polymers containing acid groups are more widely available this invention is described with reference to such a polymer in conjunction with medicaments containing basic groups. Whether the medicament contains basic or acid groups, the principle of this invention is identical.

The sheath of the microcapsules of this invention is formed from a water-insoluble film forming polymer. Any pharmaceutically acceptable polymer having reasonably good solubility in common organic solvents and low solubility in water is suitable for the sheath. Examples of suitable water-insoluble film forming polymers include methylcellulose, cellulose acetate, cellulose acetate butyrate, cellulose acetate phthalate, polyvinyl butyral, polyvinyl acetate, polymethyl methacrylate and polystyrene. A variety of other known polymers can be used.

The microcapsules of this invention are prepared by a method disclosed in the working examples. The method essentially involves the steps of (A) dispersing an aqueous solution of a water-soluble medicament-polymer salt in a solution of the water-insoluble sheath forming polymer which is dissolved in a first water immiscible organic solvent; (B) adding a second water immiscible organic solvent which is a non-solvent for the sheath forming polymer; and (C) removing the first and second solvents, e.g., by decantation or filtration and drying.

The solvents used are selected based on the nature of the water-insoluble film forming polymer. The first solvent should be a good solvent for the water-insoluble polymer and the second solvent one which is miscible with the first solvent but which is essentially a non-solvent for the polymer. Since the solvents must be removed it is advantageous if their boiling points are in a range of about 25° C. to 150° C. For example, where ethyl cellulose is used as the water-insoluble polymer toluene is a suitable first solvent and petroleum ether is a suitable second solvent.

The proportions of various materials used in forming the microcapsules of this invention in accordance with the described process can be varied widely. In general, the amount of water-soluble salt forming polymer is slightly in excess of the amount necessary to convert all of the functional groups in the medicament to the desired polymer salt form. The concentration of the medicament-polymer salt in water in the core can vary depending on the solubility of the salt in water, for instance from one to about 30% by weight. The concentration of the sheath polymer in water-immiscible solvent can also vary widely, for example, from about 5 to 40% by weight. The ratio of sheath polymer to aqueous medicament-polymer salt solution is relatively important since this ratio, in part, determines the thickness of the sheath of the microcapsule and affects the rate of release of the medicament. In general, ratios of aqueous medicament-polymer salt solutions sheath polymer can vary from 0.3:1 to 3:1. Preferably, the ratio is 0.8:1 to 1.5:1.

The volume of the second solvent (non-solvent for the sheath polymer) added to the dispersion of aqueous salt solution is generally in large excess of the volume of the dispersion. For example, the second solvent is appropriately added to the dispersion of the medicament salt in an amount of 4 to 5 times by volume of the dispersion. Preferably the initial addition of the second solvent is made slowly, e.g., dropwise. A further similar amount of the second solvent can be added rapidly and the solvents removed by decantation or filtration and drying.

The microcapsules can also be prepared by methods known in the art for encapsulating hydrophilic materials in polymer shells, for example, by the method described in U.S. Pat. No. 3,645,911, which is incorporated herein by reference.

Release times obtained with the microcapsules of this invention vary widely and depend on a number of factors such as the size of the microcapsules, the nature and thickness of the sheath resin, the concentration and nature of the medicament and salt-forming polymer and the like. However, release rates obtained with the microcapsules of this invention are significantly longer and more uniform than obtained with the corresponding unencapsulated salts formed with the same medicament and ion exchange resins or with microcapsules containing a non-polymeric salt of the same medicament. Release rates of a factor of 3 or more longer are obtained with the microcapsules of this invention compared to the corresponding forms of the medicament described above. Generally, release rates are tested, in vitro, by measuring percent release in 0.1 N hydrochloric acid (simulated stomach acid). The microcapsules of this invention tested in the foregoing manner do not release 100% of their active ingredient for at least three hours. Preferably, 100% release requires at least 6 hours and most preferably at least 12 hours. The release rates are also more uniform than are obtained with the prior art forms of the medicament described above.

The medicaments of this invention are administered to animals in a variety of oral dosage forms and can take the form of mixtures of microcapsules containing different medicaments or mixtures of microcapsules under this invention with other medicaments or active ingredients which are not microencapsulated. The dosage forms can comprise dispersions of the microcapsules in appropriate vehicles. The microcapsules can also be advantageously formed into capsules such as those made of gelatin. If appropriate measures are taken to prevent crushing the microcapsules of this invention they can be formed into tablets with suitable binders and other tableting ingredients.

This invention is further illustrated by the following Examples.

EXAMPLE 1

A solution, made by dissolving 2 g (0.013 mole) of phenylpropanolamine and 1 g (0.014 mole) of polyacrylic acid (Aldrich 18, 128-5) in 20 ml of water at 80° C., was dispersed into a solution of 20 g of ethyl cellulose (Fischer E-152) in 100 ml of toluene. Over a period of two hours, 500 ml of petroleum ether (bp 90°–110° C.) was added dropwise with rapid stirring and a second 500 ml portion of petroleum ether was added rapidly. The petroleum ether was decanted and the encapsulate was washed with two 500 ml portions of petroleum ether (bp 90°–110° C.) and four 500 ml portions of petroleum ether (bp 30°–60° C.) to give a free flowing white powder which, when observed through a microscope, appeared to consist of strings of spheres 20 to 30 microns in diameter. The release of drug from this product in 0.1 N hydrochloric acid (to simulate the acidity of the stomach) is compared in FIG. 1 with the release from an Amberlite XE 69 resin complex and from a similarly encapsulated phenylpropanolamine hydrochloride. (Amberlite XE 69 is an ion exchange resin containing acid groups available from Rohm and Haas.)

EXAMPLE 2

The procedure used in Example 1 was repeated using 30 g of ethyl cellulose.

EXAMPLE 3

The procedure used in Example 1 was repeated using 5 g of polyvinyl acetate and 5 g of ethyl cellulose in place of 20 g of ethyl cellulose. FIG. 2 compares the release rate of drug from compositions from Examples 1, 2, and 3.

EXAMPLE 4

The procedure used in Example 1 was repeated substituting 1 g of polyvinyl sulfonic acid (Air Products) for the polyacrylic acid.

EXAMPLE 5

The procedure used in Example 1 was repeated substituting 1 g of hydrolyzed Gantrez AN 169 (copolymer of methyl vinyl ether and maleic anhydride available from GAF Corporation) for the polyacrylic acid.

We claim:

1. Microcapsules comprising a core containing a water-soluble salt formed from a medicament and a water-soluble polymer, and a sheath of a water-insoluble film forming polymer wherein said salt is selected from one member of the group consisting of (1) a salt of a medicament which contains at least one basic group and a water-soluble polymer which contains at least one acid group and (2) a salt of a medicament which contains at least one acid group and a water-soluble polymer which contains at least one basic group; said microcapsules having an average particle size from about 0.5 to 50 microns.

2. Microcapsules of claim 1 in which said sheath of a water-insoluble film forming polymer comprises ethyl cellulose, cellulose acetate, cellulose acetate butyrate, cellulose acetate phthalate, polyvinyl butyral, polyvinyl acetate, polymethyl methacrylate or polystyrene.

3. Microcapsules of claim 1 wherein said water soluble polymer is polyacrylic acid, water soluble copolymer of acrylic acid and copolymerizable monomer, hydrolyzed copolymer of maleic anhydride and vinyl methyl ether, polymers or copolymers of maleic acid or fumaric acid, alginic acid, carboxymethylcellulose or polyvinylsulfonic acid.

4. Microcapsules of claim 1 having a release of less than 100% after three hours in 0.1 N hydrochloric acid.

5. Microcapsules of claim 1 in which said medicament is dextromethorphan, ephedrine, pseudoephedrine, p-aminosalicylic acid, acetaminophen and chlorpheniramine.

* * * * *